US012350661B2

(12) United States Patent
Malik et al.

(10) Patent No.: US 12,350,661 B2
(45) Date of Patent: Jul. 8, 2025

(54) OPERATION OF A MICROFLUIDIC DEVICE IN THE ANALYSIS OF SAMPLE SUBSTANCES

(71) Applicant: Bruker Daltonik GmbH, Bremen (DE)

(72) Inventors: Sven Malik, Hamburg (DE); Paul Ritter, Ostritz (DE); Klaus Wiehler, Hamburg (DE); Dirk Dammann, Hamburg (DE)

(*) Notice: Subject to any disclaimer, the term of this patent is extended or adjusted under 35 U.S.C. 154(b) by 374 days.

(21) Appl. No.: 17/207,032

(22) Filed: Mar. 19, 2021

(65) Prior Publication Data

US 2021/0291163 A1   Sep. 23, 2021

(30) Foreign Application Priority Data

Mar. 19, 2020 (DE) .......................... 102020107645.2

(51) Int. Cl.
*G01N 21/55* (2014.01)
*B01L 3/00* (2006.01)
(Continued)

(52) U.S. Cl.
CPC ....... *B01L 3/5025* (2013.01); *B01L 3/502715* (2013.01); *G01N 21/553* (2013.01);
(Continued)

(58) Field of Classification Search
CPC ............. B01L 3/5025; B01L 3/502715; B01L 2200/0636; B01L 2300/0819;
(Continued)

(56) References Cited

U.S. PATENT DOCUMENTS 7,684,024 B2   3/2010   VanWiggeren et al.
8,354,073 B2   1/2013   Oki et al.
(Continued)

FOREIGN PATENT DOCUMENTS

JP   200530905 A   2/2005
JP   2009979933 A   11/2008
(Continued)

OTHER PUBLICATIONS

Bruker Daltonics SPR, sierra SPR-32, Sep. 2018, pp. 1-12 (Year: 2018).*

(Continued)

*Primary Examiner* — Christine T Mui
(74) *Attorney, Agent, or Firm* — Benoît & Côté Inc.

(57) ABSTRACT

The invention relates to methods for operating a microfluidic device in the analysis of sample substances, comprising: (i) providing the microfluidic device, which contains an array of separate sensor spots; (ii) addressing a first selection of the sensor spots with sample substances taken up in fluid, said first selection not comprising the whole array of sensor spots; (iii) optically sensing of the first selection of sensor spots for an interaction with the sample substances; (iv) changing the operation of the microfluidic device in response to the optically sensed interaction, by addressing a second selection of the sensor spots with the sample substances taken up in fluid, said second selection not being identical to the first selection, and (v) analyzing the sample substances by optical sensing of a third selection of sensor spots which is part of the second selection. The invention likewise relates to a corresponding arrangement with microfluidic device.

20 Claims, 3 Drawing Sheets

(51) Int. Cl.
*G01N 21/552* (2014.01)
*G01N 33/553* (2006.01)
*G02B 5/00* (2006.01)
*G01N 21/00* (2006.01)

(52) U.S. Cl.
CPC ............ *G01N 33/553* (2013.01); *G02B 5/008* (2013.01); *B01L 2200/0636* (2013.01); *B01L 2300/0816* (2013.01); *B01L 2300/0819* (2013.01); *B01L 2300/0877* (2013.01); *B01L 2400/049* (2013.01)

(58) Field of Classification Search
CPC ....... B01L 2300/0877; B01L 2400/049; G01N 21/553; G01N 33/553; G02B 5/008
USPC .................................................. 422/503, 500
See application file for complete search history.

(56) References Cited

U.S. PATENT DOCUMENTS

| | | |
|---|---|---|
| 9,958,438 B2 | 5/2018 | Sjolander |
| 10,481,002 B2 | 11/2019 | Yamada |
| 2008/0268544 A1 | 10/2008 | Whalen |
| 2009/0213383 A1 | 8/2009 | Ly et al. |
| 2010/0260642 A1 | 10/2010 | Malmqvist et al. |
| 2016/0334398 A1 | 11/2016 | Weissleder et al. |
| 2020/0070164 A1 | 3/2020 | Linder et al. |

FOREIGN PATENT DOCUMENTS

| | | |
|---|---|---|
| JP | 2013525762 A5 | 5/2014 |
| JP | 2014528574 A | 10/2014 |
| JP | 2014531595 A | 11/2014 |
| WO | 200042433 A1 | 7/2000 |
| WO | 2005119210 A1 | 4/2008 |
| WO | 2008133698 A1 | 11/2008 |
| WO | 2019116296 A1 | 6/2019 |

OTHER PUBLICATIONS

Jones, A. M. et al., "A fragment-based approach applied to a highly flexible target: Insights and challenges towards the inhibition of HSP70 isoforms", Sci. Rep. 6, 34701; doi: 10.1038/srep34701 (2016).

* cited by examiner

OPERATION OF A MICROFLUIDIC DEVICE IN THE ANALYSIS OF SAMPLE SUBSTANCES

BACKGROUND OF THE INVENTION

Field of the Invention

The invention relates to methods for operating a microfluidic device in the analysis of sample substances and a corresponding set-up with a microfluidic device.

Description of the Related Art

The Prior Art is explained below with reference to a specific aspect. This shall not be understood as a limitation, however. Useful further developments and modifications of what is known from the Prior Art can also be applied above and beyond the comparatively narrow scope of this introduction, and will easily be evident to the practitioner skilled in the art in this field after reading the following disclosure.

High costs, lengthy periods of time, and low success rates in the search for pharmaceutical active agents with low molecular weight, e.g., enzymatic inhibitors or other molecules with molecular weights of s 500 atomic mass units, have led to the requirement for their activity and binding properties to be measured rapidly and accurately during the whole discovery and development process. Real time-label free (RT-LF) analysis with detection of surface plasmon resonance (SPR) has proven to be a powerful tool for biophysical characterization of low molecular weight pharmaceutical active agents and active agent candidates, and it can be carried out in high-throughput, massive parallel analyses.

The international patent application WO 2008/133698 A1, whose full content is referred to herewith for reference purposes, describes an example of a microfluidic device which can be used to carry out multiplexed analyses of this kind, and which can be operated in a process known as "hydrodynamic isolation", where highly discrete and small fluid volumes are applied at separate locations on sensor surfaces of the device for the purpose of analysis. A commercial example of such a device is the applicant's Sierra SPR™-32, with which four individually configurable sensor spots in eight parallel flow channels with individual fluid control can be addressed.

The industrial screening of fragment and low-molecular weight active agent libraries frequently involves a multistage approach, as described, for example, in the document Jones, A. M. et al. A fragment-based approach applied to a highly flexible target:Insights and challenges towards the inhibition of HSP70 isoforms. Sci. Rep. 6, 34701; doi: 10.1038/srep34701 (2016).

Preselection ("clean screen"): First, the complete library of active agents is tested for those compounds which exhibit a binding behavior that interferes with the further analysis, such as nonspecific binding to the sensor surface, even when the surface is simply bare or primed, but not coated with an immobilized analytical ligand. Each compound is tested in a single concentration with respect to all target surfaces (1-3 active surfaces per flow channel) and all reference surfaces (1-3 control surfaces per flow channel).

Single concentration screening: Secondly, the preselected library (without the interfering compounds) is tested in a single concentration with respect to all target surfaces (1-3 active surfaces per flow channel) and all reference surfaces (1-3 control surfaces per flow channel). It has been disclosed that these first two steps are performed with a single application of the active agent on several sensor surfaces, at least one of which is set up for preselection measurement. The disadvantage here is that measurement data from the analytically prepared sensor surfaces for active agents which exhibit nonspecific binding behavior on the preselection sensor surface have no informational value even for the analytically functionalized sensor spots, and therefore cannot be meaningfully evaluated. There is, furthermore, an unnecessary contamination of the analytically prepared sensor surfaces, which prevents them being used for experiments with further active agent candidates, or at least involves long washing/rinsing phases of up to one hour to rinse away the "sticky" substances bound there.

Multi-concentration screening (optional): Thirdly, all interacting active agents which exhibit the desired, favorable behavior (kinetics and binding reactions) in the single concentration screening can be tested with respect to all target surfaces (1-3 active surfaces per flow channel) and all reference surfaces (1-3 control surfaces per flow channel) in a concentration series in order to obtain detailed information on the kinetics and affinity, if required and desirable. The affinity provides particularly a measure of the strength of the bond between the active agent being tested and the functionalized sensor surface.

Given the explanations above, there is still a need for a simplified and more efficient method of operating a microfluidic device. Further objectives that can be achieved by the invention will be immediately clear to the person skilled in the art from reading the disclosure below.

SUMMARY OF THE INVENTION

The invention relates to methods for operating a microfluidic device in the analysis of sample substances, comprising: (i) providing the microfluidic device, which contains an array of separate sensor spots; (ii) addressing a first selection of sensor spots with sample substances taken up in fluid, said first selection not comprising the whole array of sensor spots; (iii) optical sensing of the first selection of sensor spots for an interaction with the sample substances; (iv) changing the operation of the microfluidic device, depending on the optically sensed interaction, by addressing a second selection of sensor spots with the sample substances taken up in fluid, said second selection not being identical to the first, and (v) analyzing the sample substances by optical sensing of a third selection of sensor spots which is included in the second selection.

In various embodiments, groups of sensor spots arranged in series can be combined to form parallel flow channels, which can be addressed together or individually with sample substances taken up in fluid. In the context of this disclosure, the term "addressed" means that the fluid containing the sample substance(s) comes into contact with the sensor spot(s), by the fluid flowing over the sensor spot(s), for example. It is preferable for each flow channel to have at least one sample substance injection device which can be individually (de-)activated. In various embodiments, a different sample substance taken up in fluid can be applied via the corresponding sample substance injection device(s) in each flow channel. Usually, the series of sensor spots in one flow channel are each framed by a running buffer injection port and a running buffer extraction port. When the microfluidic device is in operation, the running buffer passes through all the sensor spots and carries with it any admixed sample substance fluids in the direction from injection to extraction port. For this reason, the running buffer can also be called guiding fluid. The running buffer or guiding fluid also brings about hydrodynamic isolation of the neighboring flow channels, i.e., there is no crossover of sample substance fluid from one flow channel to the next.

In various embodiments, a sample substance extraction device which can be individually (de-)activated can be assigned to each sensor spot. In certain embodiments, the devices assigned to the sensor spots can be designed such that they can both inject and extract fluid. It is thus possible and conceivable to use specific sample substance injection devices as the sample substance extraction device in specific phases of the method, e.g., when testing the nonspecific interaction on the sensor spots of the first selection, and to actually use them as the sample substance injection device in other phases of the method (before and/or afterwards), e.g., in kinetics or affinity studies.

It is preferable for at least one sensor spot of each flow channel to belong to the first selection, and for at least one further sensor spot of each flow channel to belong to the third selection. The first and second selections denote those sensor spots over which the sample substances taken up in fluid are guided at various stages during the process. The third selection of sensor spots, in contrast, does not denote a specific addressing of sensor spots with sample substance fluid, but instead determines the evaluation of data which were detected by the corresponding sensor spots during the optical analytical sensing, preferably simultaneously with an imaging method. The sensing may particularly comprise irradiation of the sensor spots with electromagnetic waves, e.g., light, and simultaneous detection of the portion of the electromagnetic waves reflected by the sensor spots and their characteristics. It is most preferable to scan several sensor spots simultaneously, from several flow channels or across several flow channels, where applicable, for example with an optical imaging method. This accelerates the acquisition and processing of the data.

In various embodiments, if the optically sensed interaction produces a positive result on the sensor spot(s) belonging to the first selection, it is possible for the sample substance injection device of the flow channel concerned to be deactivated for the purpose of addressing the second selection of sensor spots. In this way, the very non-specifically binding, "sticky" active agents and active agent candidates can be excluded from further analyses, which will very likely have no informational value, thereby preventing the other sensor spots in this flow channel from being exposed to these interfering substances.

If all the injected sample substances on the sensor spots of the first selection exhibit a non-negligible interaction, i.e., particularly if they are all "sticky", this would mean that further analyses of the affinity/interaction on the sensor spot surfaces are superfluous because they cannot be expected to yield any information. This, of course, constitutes a criterion for termination. In such a case, the fluid feed for the entire device could be stopped, and a new set of sample substances would be required. Nevertheless, in such a case, the sensor spots of the second selection which do not belong to the first selection (in other words the disjunct portions of the first and second selection) are still untouched and can therefore be addressed in further experiments. In specific embodiments, the microfluidic device would therefore not necessarily have to be newly set up, for example by changing the chip which carries the sensor spots. Instead, other sensor spots could be identified for the testing of nonspecific interaction or binding of new active agents and active agent candidates, provided unused sensor spot surfaces are still available.

In further embodiments, the second selection of sensor spots can be addressed where the optically sensed interaction on the sensor spot(s) belonging to the first selection produces a negative result by activating the sample substance extraction device behind a last sensor spot of a flow channel, with simultaneous deactivation of the other sample substance extraction devices in this flow channel, if present. If the sensor spots between the sample substance injection device and the last sample substance extraction device in a flow channel are in a linear arrangement, then in this case the injected fluid flows over all the sensor spots of the flow channel and the binding/affinity properties of the sample substances can be investigated. The expression "not identical" in the context of the present disclosure shall mean that the first selection and the second selection, or the quantities of sensor spots on which these selections are based, are not identical, although they can overlap. For example, it is possible that the first selection is completely included in the second selection of sensor spots, namely if the optically sensed interaction produces a negative result for all sensor spots of the first selection, so that all the sample substances injected are suitable for more detailed analyses because of their lack of nonspecific binding. However, it is also conceivable that the first and the second selection of sensor spots do not exhibit any matches, i.e., they are completely disjunct, for example if the sample substances for the interaction measurement and the analytical measurement are injected only onto those sensor spots, or in other words, only those sensor spots are addressed with sample substance fluid, from which correspondingly informative measurement data can be evaluated for the relevant test, i.e., sensor spots with non-functionalized or analytically functionalized surfaces respectively.

In various embodiments, the analysis can comprise the optical sensing of a single concentration as well as a concentration series of the sample substances taken up in fluid. It is thus possible to obtain more detailed information on kinetics and affinity for the individual active agents and active agent candidates. The measuring time for a single concentration can be between half a minute and ten minutes, depending on the experimental setup. It is possible to exploit the fact that the various sample substances bind to the immobilized ligands on the analytically functionalized surfaces and can separate again as the fluid feed continues with a reduced quantity of sample substance, possibly down to zero admixing, i.e., the sample substances can, in particular, be rinsed off or washed off. In this way, sequential phases of binding and also separation of the bond can be recorded by optical sensing and evaluated.

The sensor spots which do not belong to the first selection can contain analytically functionalized surfaces. Analytically functionalized surfaces can be coated, for example, with activated, or activated and blocked, dextran (e.g., in the carboxymethylated state), polycarboxylates or alkanethiols (in a self-assembled monolayer, SAM) as the reference surface. Resonance signals from these primed areas particularly allow a baseline subtraction. It is also possible in principle to coat the sensor spots of the first selection with a primer such as dextran or similar substances. The occurrence of a nonspecific interaction can also be tested in respect of dextran surfaces (or similar primers). It is preferable for the analytically functionalized surfaces, especially the sensor spots of the second selection, to have a layer of immobilized ligands for the actual analytical analyses, for example enzymes, antibodies, structural proteins, and/or other biomolecules. Of interest is the behavior toward serum proteins such as human serum albumin (HSA) and alpha- 1-acid glycoprotein (AGP), for example. Depending on the task in hand, the immobilized ligands can differ from each other or be the same for each sensor spot, particularly in one flow channel.

In various embodiments, the optical sensing can detect an affinity or interaction of the sample substances with the sensor spot surfaces. In particular, the optical sensing can detect surface plasmon resonance in which the (selected) sensor spot surfaces are irradiated by light, and the light reflected from the surfaces can be detected, in particular such that several sensor spots can be simultaneously monitored in the form of a massive parallel analysis, e.g., with an optical imaging method. The microfluidic device can comprise a prism for the optical passage of electromagnetic waves, where one lateral face of the prism, which is provided for contact with the fluid, carries the array of sensor spots. Alternatively, it is also possible to design the microfluidic device such that it has a glass plate resembling a specimen slide, one side of which can be brought into contact with a prism surface for the optical passage of electromagnetic waves, and its other side is designed for making contact with the fluid by virtue of the configuration of the array of sensor spots. The prism and/or glass plate can be designed as a chip made of consumable material or reusable material.

The invention likewise relates to an arrangement for the analysis of sample substances, comprising: (a) a microfluidic device which contains an array of separate sensor spots, and each sensor spot can be addressed by sample substances taken up in fluid (individually or in groups); (b) a sensing device which can optically scan the sensor spots or a selection thereof; and (c) a control system which communicates with the microfluidic device and the sensing device and is also designed and configured to execute the following steps: (i) control the microfluidic device such that a first selection of sensor spots which does not comprise the complete array is addressed by sample substances taken up in fluid; (ii) control the sensing device such that the first selection of sensor spots is optically sensed for an interaction with the sample substances; (iii) control the microfluidic device such that its operation is changed, depending on the optically sensed interaction, by addressing a second selection of sensor spots with the sample substances taken up in fluid, said second selection not being identical to the first; and (iv) control the sensing device such that the sample substances are analyzed by optical sensing of a third selection of sensor spots, which are included in the second selection.

It shall be understood that the various designs and embodiments described above for the method disclosed can be realized in the same way in the arrangement with a microfluidic device, particularly with regard to their operating mode. It is therefore not necessary to repeat it.

BRIEF DESCRIPTION OF THE DRAWINGS

The invention can be better understood by referring to the following illustrations. The elements in the illustrations are not necessarily to scale, but are primarily intended to illustrate the principles of the invention (mostly schematically). In the illustrations, the same reference numbers designate corresponding elements in the different views.

DETAILED DESCRIPTION

While the invention has been illustrated and explained with reference to a number of embodiments, those skilled in the art will recognize that various changes in form and detail can be made without departing from the scope of the technical teaching, as defined in the attached claims.

Figure 1:
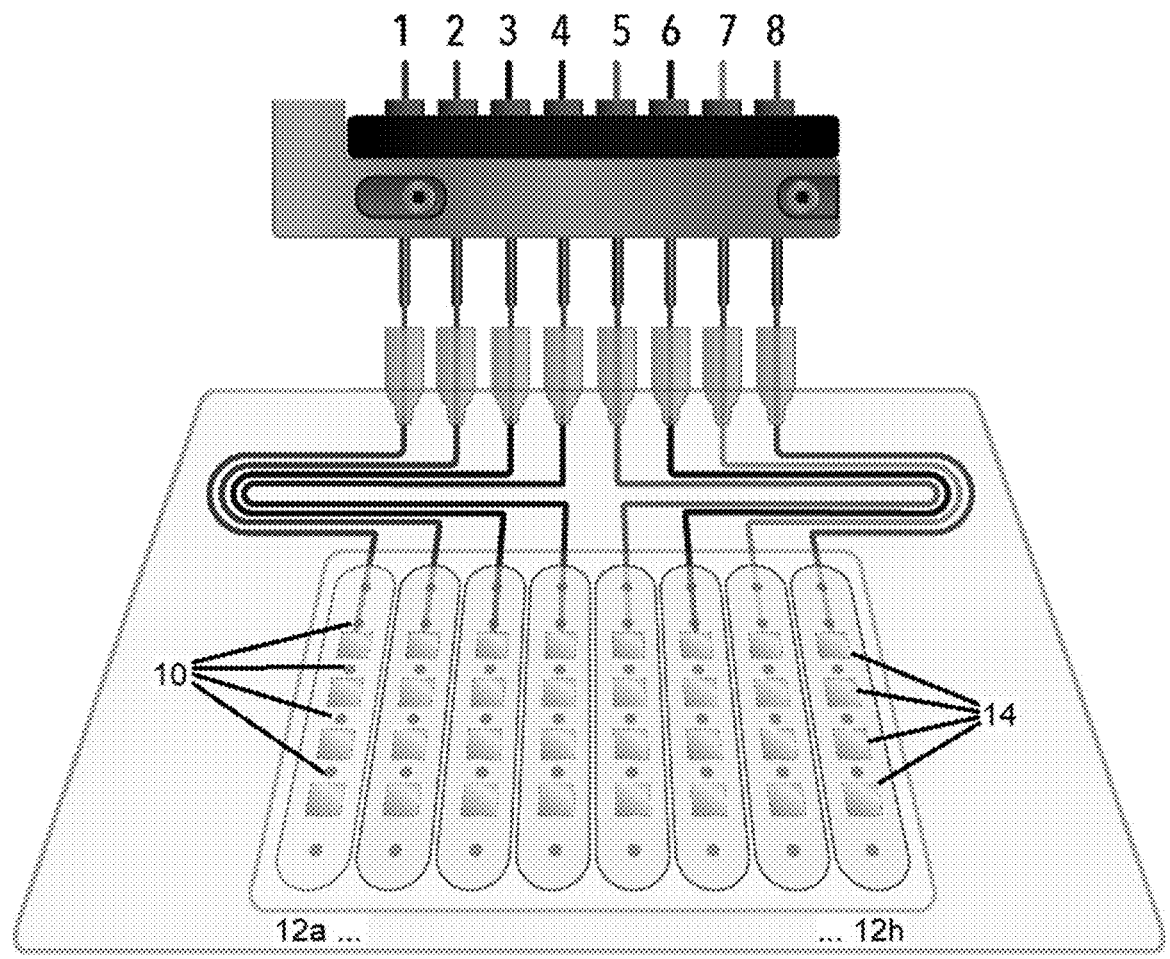
FIG. 1 is a schematic view of a microfluidic device with a number of flow channels and an autosampler.

FIG. 1 is a schematic representation of an arrangement with a microfluidic device which is suitable for performing the method disclosed. The arrangement comprises an autosampler with eight fluid feeds (1-8), which can be controlled in parallel and independently of each other. Each fluid feed can supply an individual active agent or active agent candidate from a library of active agents in a suitable buffer solution for analysis, said solution being introduced into the eight parallel flow channels (12a-h) via injection needles and suitably assigned injection ports (10). The buffer solution may contain an organic solvent such as dimethyl sulfoxide (DMSO), for example.

In the example illustrated, the microfluidic device contains 32 sensor spots (14), which are arranged in an 8×4 grid so that four sensor spots (14) in one flow channel (12a-h) are assigned to each of the eight fluid feeds (1-8), and each can be addressed individually. Eight samples can therefore be fed simultaneously to the sensor spots (14) via the microfluidic device explained above. For real-time sensing of the affinity or interaction of the active agents and active agent candidates (WS) admixed to the buffer solution (PL) with the sensor spot surfaces, which may be primed, analytically functionalized with ligands (LIG), or otherwise activated and possibly blocked, a highly sensitive surface plasmon resonance imaging detector can be used, for example from the SPR+ series manufactured by the applicant. The measurement principle is summarized schematically for reasons of clarity in FIG. 2.

The combination of SPR imaging (SPRi) with a high-intensity laser light source (LLQ) and optical high-speed scanning by acousto-optical deflector (AOD), as described in the U.S. Pat. No. 7,684,024 B2 of the applicant, whose entire content is referred to herewith for reference purposes, allows high-sensitivity sensing. This arrangement supports the extremely sensitive imaging of relatively large, two-dimensional sensor spot arrays, while the intensity of the light source allows a high-speed camera (HGK) to be used, which in turn records a large number of resonance measurements per scan. The scanning rate can be selected in the range between 0.1 and 100 hertz, for example. This makes it possible to achieve a signal-to-noise ratio of 0.02 resonance signal units (root mean square, RMS) and better precision in the measurement of small reaction changes, which can frequently be observed for fragment or binding experiments with pharmaceutical active agents and active agent candidates of low molecular weight.

The SPR measurement principle, which is familiar to those skilled in the art, shall be briefly explained here again. In the case of the total reflection of light which is incident on a surface, for example the interior surface of a prism (PR) as shown, or the interior surface of a glass plate resembling a specimen slide which is brought into contact with a prism, a so-called evanescent field is generated, which has a limited penetration depth of around 300 nanometers. If the resonance conditions are fulfilled, the evanescent field is able to interact with surface plasmons of a thin metal film on the side of the surface pointing away from the incident light, usually the corresponding exterior surface of the prism (PR) or the glass plate, which can be gold or silver-plated, for example. The resonance conditions arise as a function of the following parameters: (a) angle of incidence, (b) refractive index and (c) wavelength. The wavelength is not usually changed during an experiment. Thus, changes to the refractive index near the surface of the metal film can be detected by the change in the resonance angle. Since the binding of molecules to the surface leads to a change in the refractive index, the binding of active agents and active agent candidates can be measured and displayed with temporal resolution.

The sensor spots used in SPR systems can be located on a gold-plated or otherwise metallized surface of a prism (PR) or a glass plate resembling a specimen slide, which is mounted on a module which can be moved manually. The metal film surface required for SPR can be coated with a self-assembled monolayer in order to block nonspecific binding of proteins, for example, and to facilitate binding of molecules to the surface.

Figure 2:
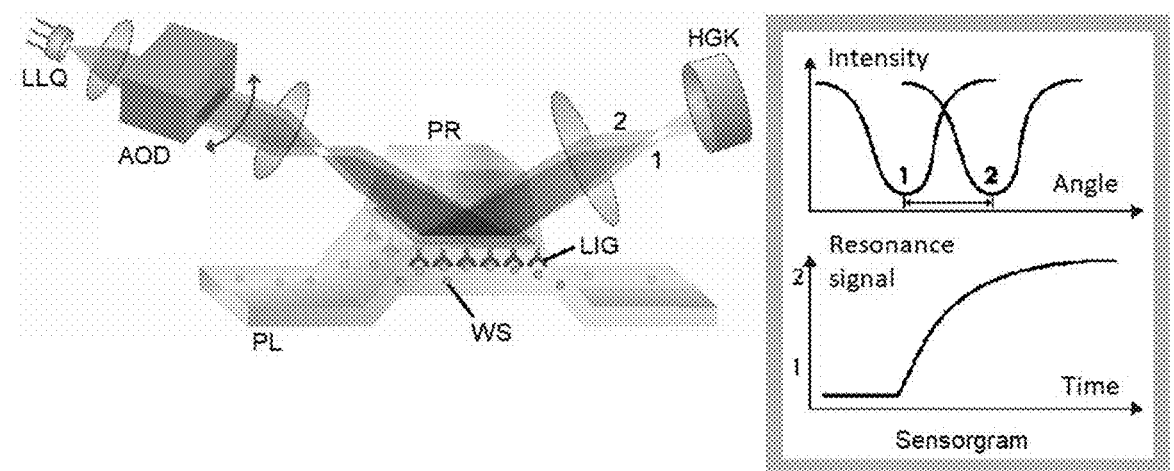
FIG. 2 is a schematic diagram of a surface plasmon resonance measurement over a range of different angles of incidence and reflection of the light.

The resulting sensorgram is a diagram of the surface plasmon resonance signal in resonance units (RU) as a function of time (FIG. 2, bottom right). One resonance unit corresponds to the binding of one picogram of substance to the surface of a sensor spot with an area of one square millimeter (pg/mm$^2$). The sensitivity is such that admixtures of sample substances in the carrier fluid can be detected right down to the micromole range.

Figure 3:
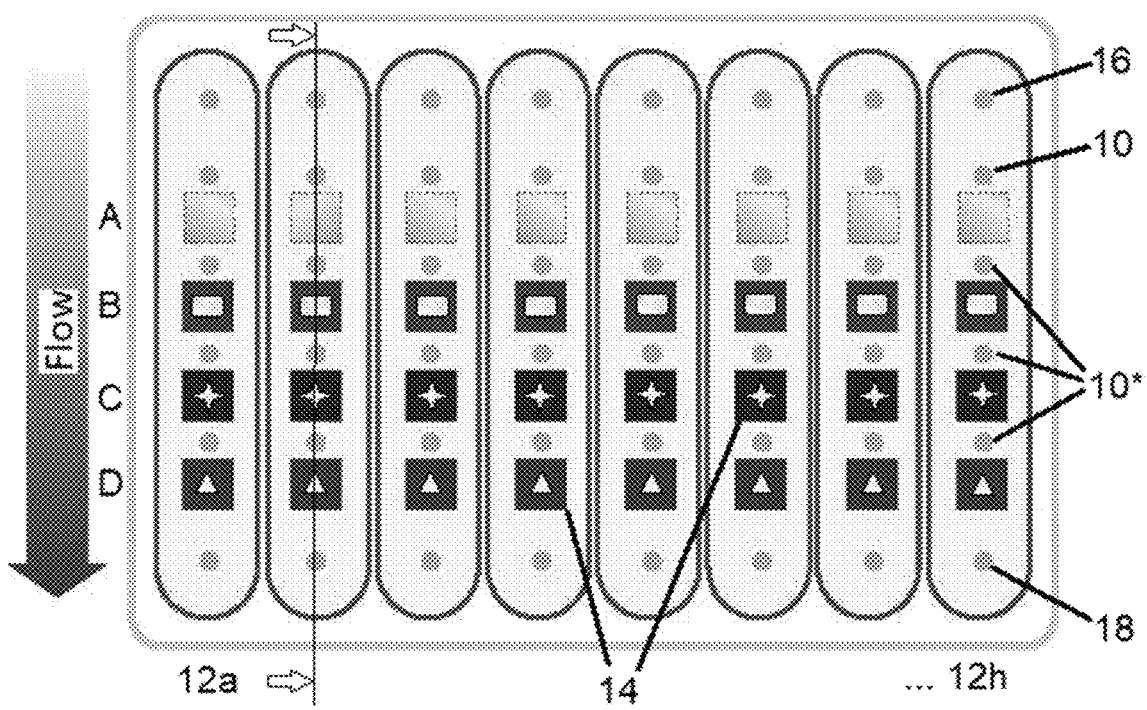
FIG. 3 is a schematic top view of the flow channels in a section of a microfluidic device similar to that of FIG. 1.

FIG. 3 is a schematic of the sensor spot arrangement on the example microfluidic device in an enlarged top view. In this example, the sensor spots (14) in the individual flow channels (12a-h) are grouped in rows (ABCD) and uniformly prepared with ligands and/or coatings in these rows (illustrated by symbols on the surfaces or absence of symbols). Of the four sensor spots (ABCD) assigned to each flow channel (12a-h), two are provided with different analytical ligands (CD), while one row (A) in each case is completely untreated, i.e., comprises an untreated metal surface, for example a gold or silver-plated surface, or at most is primed with dextran, polycarboxylates or alkanethiols (in a self-assembled monolayer), and one row (B) can in each case be activated and blocked for control purposes, for example with carboxymethylated dextran. It shall be understood that an experiment also allows other configurations of the sensor spots (14) in the individual flow channels (12a-h). For example, it is not necessary to form uniform rows, but instead the selection of ligands and/or other coatings for testing can be non-uniform. The fact that it is possible to individually address the separate sensor spots (14) in each flow channel (12a-h) allows varied experimental setups to be realized.

A target protein can, for example, be bound and immobilized to the sensor spots (14) located in row (D) with the aid of the standard chemistry for the immobilization of primary amines. The sensor spots (14) in row (C) of each flow channel (12a-h) can be analytically functionalized with a reference protein and used as control spots. To create a secondary control spot, the sensor spots (14) in row (B) can be activated and blocked in each flow channel (12a-h). Test conditions can, for example, comprise immobilization of the target and reference proteins with a PBS buffer (PBS, phosphate-buffered saline), which contains 0.05% of a polysorbate 20, such as the TWEEN™20 tenside (pH 7.4). The active agent candidates, on the other hand, can be tested in a PBS buffer which contains 0.05% TWEEN™ 20 and 3% DMSO (pH 7.4) at 25° C.

The sample substance injection device has a sample substance injection port (10) for each flow channel (12a-h) in the microfluidic device shown. Each port is located at the front end of the column of sensor spots (14) (in front of row (A)) and serves to introduce fluid enriched with sample substances into the flow channels (12a-h). The sample substance injection port (10) can be flanked by corresponding injection ports (16) for running buffer or guiding fluids, which have no analytical significance and serve to guide the flow of analytical fluid and to hydrodynamically isolate the flows in adjacent flow channels (12a-h). In this example, the injection ports (16) are located at the top end of the flow channels (12a-h). On the other hand, corresponding extraction ports (18) for running buffer/guiding fluid can be located at the end of the respective flow channels (12a-h). Any fluid which has flowed from top to bottom in the illustration across the individual sensor spots (14) can be removed from the flow channels through the extraction ports (18) at the latest. This extraction can be accelerated and improved by operating a pump which extracts the fluid, for example.

Further sample substance extraction ports (10*) are located between the individual sensor spots (14) and can be controlled individually. Depending on whether the control activates or deactivates these ports, they determine how many sensor spots (14) of a flow channel (12a-h) the sample substance fluid introduced simultaneously will flow across. In certain designs of the device, the downstream ports (10*) can be used for both sample substance injection and extraction. Individual sensor spots (14), for example only (A), (B), (C) or (D), or groups of sensor spots (14), for example (ABCD), (ABC), (AB), (BCD), (BC) or (CD), can thus be specifically addressed with sample substance fluid. If all but one sample substance injection/extraction ports of a flow channel (12a-h) are deactivated for fluid injection in the direction of flow, the fluid containing the sample substance under analysis flows over all downstream sensor spots (14) of a flow channel (12a-h) and allows (analytical) interactions with all these sensor spots (14), which can be observed by means of parallel sensing (imaging), for example.

In a preferred embodiment of the operation of the microfluidic device, the active agents and active agent candidates in fluid which are being tested are guided across only a subset of the sensor spots (14) contained in a flow channel (12a-h), where they can be tested for nonspecific binding to the bare or only primed surface of the sensor spot, e.g., a metal surface or a surface coated with dextran. In the example explained here, the sensor spots (14) from the first row (A) are to be selected to check this nonspecific interaction and therefore do not comprise a special, analytically informative surface coating (first selection). If some of the sample substances prove to be particularly "sticky" despite the surface coating, this property could have a detrimental effect on the informational value of the test results for the interaction with respect to immobilized ligands or otherwise analytically functionalized sensor spot surfaces. In the context of an SPR measurement, an active agent or active agent candidate can be deemed to be nonspecifically binding or "sticky" when the resonance signal is more than 10-20 RU even without special surface treatment of the sensor spot in the first selection, for example directly on the metal film surface of an SPR sensor spot or a metal surface simply primed with dextran, polycarboxylates or alkanethiols (in a self-assembled monolayer), for example.

For testing purposes, the sample substance extraction port behind the first sensor spot (14) in a row (A) is activated, assisted where necessary by an extraction pump (not shown), so that the sample substance taken up in the fluid does not flow over the other sensor spots (B-D) in a first step. Simultaneously, the first sensor spots (14) are optically scanned for binding behavior, e.g., in parallel with SPRi, and evaluated in real time, as illustrated schematically in FIG. 2. A control system (not shown), e.g., an appropriately programmed microprocessor or comparable computational unit, receives the results of this first optical sensing and deactivates the fluid feed to the sample substance injection ports (10) of those flow channels (12a-h) where nonspecific binding behavior is detected, for example because a preset threshold of resonance units (RU) is exceeded. The other sensor spots (14) in these flow channels (12a-h), from which no further informative analytical information can be expected in the case of "sticky" sample substances, remain unused or clean in the further analysis and can be addressed with other active agents and active agent candidates in subsequent experiments.

In a continuous transition from this preselection to single concentration screening, the next step is that the control system activates those sample substance extraction ports which are located behind the last row (D) of sensor spots (14) and simultaneously deactivates the sample substance extraction port behind the first row (A) of sensor spots (14) which served to scan the interaction, so that not only the sensor spots (14) in row (A) but also those in rows (BCD) are addressed with sample substance fluid (second selection). In this example, the respective sample substance taken up in fluid now flows over all sensor spots (14) located in one flow channel (12a-h) and downstream of row (A), and these spots can be scanned for their analytical properties, i.e., activated/blocked sensor spots in row (B), control spots in row (C), and the actual target protein spots in row (D), for example. If deemed necessary, measurement of a concentration series for the sample substances which do not bind nonspecifically to the surfaces can then be carried out in order to obtain more detailed information on the kinetics and the affinity. This measurement is preceded by a rinsing and washing phase, in which running buffer flows over the previously addressed sensor spots (14) so that any sample substance residues bound thereto are removed from the sensor spot surfaces.

Figure 4A:
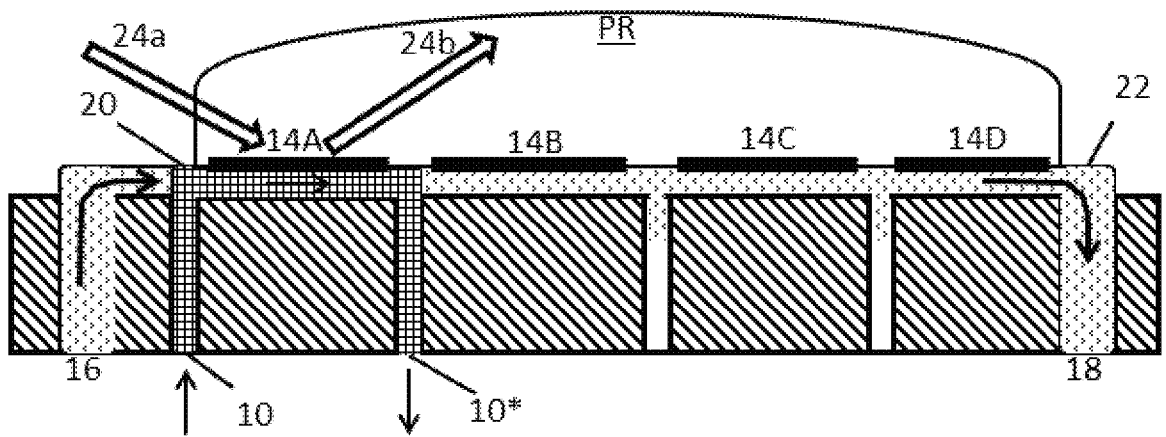
FIG. 4A shows a first step of a process of addressing various sensor spots of a flow channel in a microfluidic device with (sample substance) fluid in cross-section.
Figure 4B:
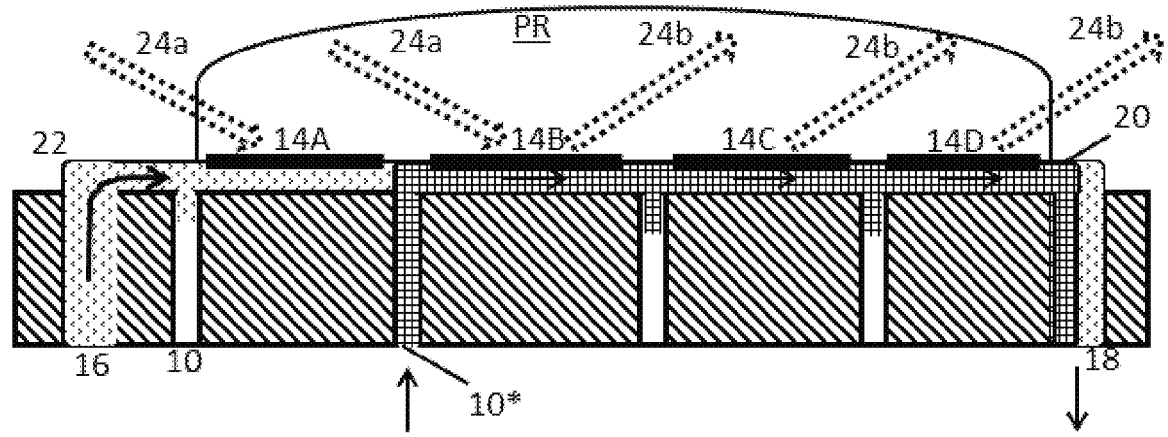
FIG. 4B shows a second step of the aforementioned process.
Figure 4C:
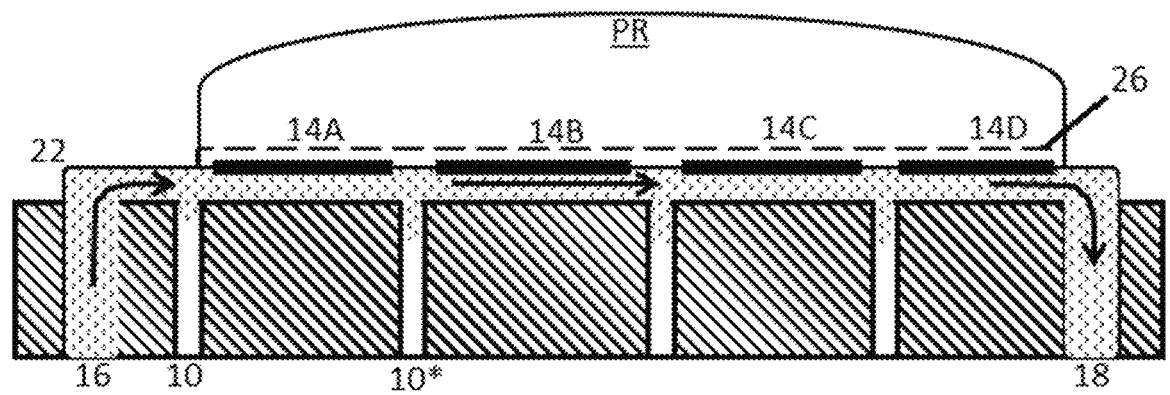
FIG. 4C shows a third step of the aforementioned process.

FIGS. 4A-C show an example sequence in several steps in a schematic cross-section through the second flow channel (12b) from FIG. 3, as indicated by the thin line and the two direction of sight arrows.

FIG. 4A shows how a sample substance fluid (20), i.e., a suitable solvent which has been enriched with the active agent or active agent candidate, is injected through the first sample substance injection port (10) into the microfluidic device, where it is admixed to a running buffer or guiding fluid (22), which originates from the first and largest injection port (16) and flows along the whole length of the flow channel (12b) to a rear extraction port (18), where it is removed from the fluid cycle, assisted by an extraction pump (not shown), where necessary. The running buffer or guiding fluid (22) can be introduced into each of the parallel flow channels (12a-h) and provides hydrodynamic isolation of the sample substance fluids (20) admixed in the various flow channels (12a-h), i.e., the sample substances cannot mix and affect each other across the flow channels (12a-h). The sample substance extraction port (10*) following directly after a first sensor spot (14A) is activated in this method phase, assisted by an extraction pump where necessary, so that the sample substance fluid (20) is removed from the fluid cycle again here without coming into contact with the sensor spots (14B-14D) located further downstream. Only the running buffer or the guiding fluid (22) flows to the end of the flow channel (12b), but this does not affect the other sensor spots (14A-14D), except by rinsing away any previously bound substances in a cleaning process. It shall be understood that the sample substance extraction port (10*) only functions as such in this step. In other phases of the method, it can also function as a sample substance injection port, as explained hereinafter.

In this example, a prism (PR) takes the form of a chip carrying sensor spots, and on one lateral face it comprises the four sensor spots (14A-14D) of the second flow channel (12b), shown in black in this sectional view. The other flow channels (12a, 12c-h) are each located either in front of or behind the image plane from FIG. 4A. Light (24a) is projected through the prism onto the sensor spots (14A-14D) in order to detect any nonspecific binding of the sample substances to the sensor spot surfaces in the light reflected from there (24b). Using an imaging method, all sensor spots (14A) assigned to the first row (A) of the flow channels (12a-h) can be simultaneously analyzed for nonspecific binding behavior.

There are then essentially two scenarios: (i) The test from the first sensor spot (14A), which does not have any special, analytically significant surface coating, shows no indication of nonspecific binding, so the corresponding active agent or active agent candidate can be tested for its kinetics and/or affinity in respect of the remaining sensor spot surfaces (14B-14D), which have been analytically functionalized in a desired way. A possible continuation of the step shown in FIG. 4A is illustrated in FIG. 4B for this case. In this example, the first sample substance injection port (10) is deactivated, the second sample substance injection/extraction port (10*) is switched over from sample substance extraction mode to sample substance injection mode. The other sample substance injection/extraction ports in front of the rear extraction port (18) remain in the "idle" state. Operation of the running buffer or guiding fluid also remains unchanged so that it flows through the entire flow channel (12b), from the front injection port (16) to the rear extraction port (18). The sample substance fluid (20) is thus guided over the sensor spots (14B-14D), where it is scanned for its kinetics and/or interaction by projecting light (24a) and detecting its reflected portion (24b) by optical means.

In an alternative embodiment to FIG. 4B, the first sample substance injection port (10) could remain activated so that the sample substance fluid (20) flows over all the sensor spots (14A-14D). This approach would not have a detrimental effect on the downstream sensor spots (14B-14D). The optical sensing could then nevertheless simultaneously scan the whole array of sensor spots in an imaging method, although evaluation of the analytically relevant information would not need to include the sensor spots of row (A) because they lack analytically relevant content.

(ii) The test from the first sensor spot (14A) can also produce indications of nonspecific binding, for example by a maximum threshold of resonance signal units being exceeded, with the result that the corresponding active agent or active agent candidate on the other sensor spot surfaces (14B-14D), which have been analytically functionalized in a desired way, would not provide any informative results in studies of kinetics and/or affinity. In this case, it is possible in principle to stop the fluid feed for the relevant flow channel (12b) in general, although the test measurements in the adjacent flow channels, in which no nonspecific binding has occurred, can naturally be continued. As an alternative, it is also possible to start a rinsing cycle in the flow channels with "sticky" sample substances, while in other flow channels the kinetics and/or affinity studies are continued in parallel. This procedure is illustrated in FIG. 4C. For the rinsing, no sample substance fluid (20) is injected via any injection port (10, 10*). Instead, only the running buffer or the guiding fluid (22) flows over the entire length of the flow channel (12b) and thereby removes any bound substances. It shall be understood that such a rinsing cycle can also be inserted into other phases of the method.

The broken line (26) in FIG. 4C is intended to illustrate that the sensor spots (14A-14D) do not necessarily have to be arranged on the bottom surface of a prism (PR), but can be located on a separate glass plate, which is placed between the bottom of the prism (PR) and the part of the microfluidic device that forms the flow channel. In the latter case, less material is used for the element supporting the sensor spot when it is designed to be consumable material, i.e., for single use. In this case, the prism could be used several times even without time-consuming cleaning steps.

The invention has been described with reference to a number of different embodiments. However, those skilled in the art will understand that various aspects or details of the invention can be modified, or various aspects or details of the different embodiments can be combined as desired, where feasible, without deviating from the scope of the enclosed claims. Flow channels with more or fewer than four sensor spots can be formed, for example. The number of flow channels in the microfluidic device can also be varied from one to a number greater than eight. In general, the foregoing description is for the purpose of illustration only, and not to limit the invention, which is defined solely by the enclosed claims, including any possible equivalent designs.

The invention claimed is:

1. A method for operating a microfluidic device in the analysis of sample substances, comprising:
providing the microfluidic device, which contains an array of separate sensor spots, wherein groups of sensor spots arranged in series are combined to form parallel flow channels, which are addressed together or individually with sample substances taken up in fluid;
providing a plurality of switchable extraction flow paths in at least one of the parallel flow channels, including (i) a first extraction flow path for extracting sample substances that have passed over a first selection of sensor spots in the at least one of the parallel flow channels, said first selection of sensor spots not comprising all sensor spots in the at least one of the parallel flow channels, and (ii) a second extraction flow path for extracting sample substances that have passed over a second selection of sensor spots in the at least one of the parallel flow channels, the second selection of sensor spots not being identical with the first selection of sensor spots;
addressing the first selection of sensor spots with sample substances taken up in fluid using the first extraction flow path;
optically sensing of the first selection of sensor spots for indicating occurrence or non-occurrence of nonspecific binding or nonspecific interaction between the sample substances and the first selection of sensor spots;
changing a mode of operation of the microfluidic device in response to an optically sensed nonspecific binding or nonspecific interaction indicated as not having occurred to switch the first extraction flow path to the second extraction flow path, and to address the second selection of sensor spots with the sample substances taken up in fluid; and
analyzing the sample substances by optically sensing of a third selection of sensor spots which is part of the second selection, wherein at least one sensor spot of the at least one of the parallel flow channels belongs to the first selection, and at least one further sensor spot of the at least one of the parallel flow channels belongs to the third selection.

2. The method according to claim 1, wherein a group of sensor spots arranged in series and combined to form one of said parallel flow channels comprises four sensor spots.

3. The method according to claim 1, wherein each flow channel has at least one sample substance injection device which can be individually activated and deactivated.

4. The method according to claim 1, wherein a different respective sample substance taken up in fluid is introduced into each flow channel via a corresponding sample substance injection device.

5. The method according to claim 1, wherein a sample substance extraction device which can be individually activated and deactivated is assigned to each sensor spot.

6. The method according to claim 1, wherein a total number of said parallel flow channels is eight.

7. The method according to claim 3, wherein the second selection of sensor spots is addressed by deactivating the sample substance injection devices of flow channels for which an optically sensed interaction on the sensor spot or spots belonging to the first selection in each case produces a sensing result indicating that nonspecific binding or nonspecific interaction has occurred.

8. The method according to claim 5, wherein for addressing the second selection of sensor spots where the optically sensed interaction on the sensor spot or spots belonging to the first selection produces a sensing result indicating that nonspecific binding or nonspecific interaction has not occurred, the sample substance extraction device associated with a last sensor spot of a selected flow channel is activated with simultaneous deactivation of any other sample substance extraction devices in the selected flow channel.

9. The method according to claim 1, wherein said analysis comprises an optical sensing of a single concentration and a concentration series of the sample substances taken up in fluid.

10. The method according to claim 1, wherein the sensor spots of the first selection comprise bare metal surfaces and/or surfaces primed with a predetermined primer.

11. The method according to claim 1, wherein the sensor spots which are not part of the first selection comprise analytically functionalized surfaces.

12. The method according to claim 11, wherein the analytically functionalized surfaces have a layer of immobilized ligands.

13. The method according to claim 12, wherein the immobilized ligands are different for each sensor spot.

14. The method according to claim 1, wherein the optical sensing detects an affinity or interaction of the sample substances with sensor spot surfaces.

15. The method according to claim 1, wherein the optical sensing detects a surface plasmon resonance behavior.

16. The method according to claim 15, wherein the nonspecific binding or nonspecific interaction is indicated by a maximum threshold of resonance signal units being exceeded.

17. The method according to claim 16, wherein the maximum threshold is selected from the range of 10-20 resonance signal units.

18. The method according to claim 1, wherein, when said optical sensing indicates occurrence of nonspecific binding in a first of said parallel flow channels, a running buffer is guided over the entire length of said first parallel flow channel and thereby removes any bound substances.

19. The method according to claim 12, wherein the immobilized ligands comprise at least one of enzymes, antibodies, structural proteins, and other biomolecules.

20. The method according to claim 1, wherein the optical sensing comprises an optical imaging method which scans a plurality of sensor spots simultaneously across a plurality of the parallel flow channels.

* * * * *